United States Patent [19]
Michelotti et al.

[11] Patent Number: 5,811,427
[45] Date of Patent: Sep. 22, 1998

[54] HETEROCYCLIC N-ACETONYLBENZAMIDES

[75] Inventors: Enrique Luis Michelotti, Fort Washington; David Hamilton Young, Ambler, both of Pa.

[73] Assignee: Rohm and Haas Company, Philadelphia, Pa.

[21] Appl. No.: 877,945

[22] Filed: Jun. 18, 1997

Related U.S. Application Data

[60] Provisional application No. 60/020,518 Jun. 28, 1996.

[51] Int. Cl.[6] .............. C07D 401/02; C07D 403/02; A61K 31/435; A61K 31/495
[52] U.S. Cl. .............. 514/255; 514/258; 514/300; 514/301; 514/302; 514/432; 514/443; 514/469; 544/253; 544/278; 544/350; 546/113; 546/114; 546/115; 546/121; 546/278; 549/23; 549/49; 549/396
[58] Field of Search .............. 514/399, 255, 514/258, 300, 301, 302, 432, 493, 469; 548/310.1; 544/253, 278, 350; 546/113, 114, 115, 121, 278; 549/23, 49, 396

[56] References Cited

U.S. PATENT DOCUMENTS

| | | |
|---|---|---|
| 3,661,991 | 5/1972 | McNulty et al. . |
| 3,709,897 | 1/1973 | McNulty et al. . |
| 4,822,902 | 4/1989 | Carley et al. ............... 558/14 |
| 5,075,471 | 12/1991 | Michelotti et al. ............ 556/144 |
| 5,304,572 | 4/1994 | Michelotti et al. . |
| 5,453,531 | 9/1995 | Seitz et al. ............... 560/29 |
| 5,514,719 | 5/1996 | LaTorse et al. ............ 514/622 |

FOREIGN PATENT DOCUMENTS

| | | | |
|---|---|---|---|
| 566020 | 4/1993 | European Pat. Off. ............ 514/399 |

OTHER PUBLICATIONS

Ries et al, Chemical Abstracts, vol. 120, No. 13, Abstract No. 164, 185, p. 1186, Mar. 24, 1994.

Equivalent to EP 566,020.

*Primary Examiner*—Zinna Northington Davis
*Attorney, Agent, or Firm*—Guy T. Donatiello

[57] ABSTRACT

Certain N-acetonylbenzamides and their use as fungicides are disclosed. The N-acetonylbenzamides disclosed contain a heterocyclic ring fused to an aromatic ring. These compounds are particularly effective against phytopathogenic fungi of the class Oomycetes. Also disclosed is a method for controlling phytopathogenic fungi by applying one or more of the heterocyclic N-acetonylbenzamides of the present invention, optionally with one or more additional fungicidal compounds.

16 Claims, No Drawings

HETEROCYCLIC N-ACETONYLBENZAMIDES

This application is based on provisional application 60/020,518 filed Jun. 28, 1996.

The present invention relates to certain heterocyclic N-acetonylbenzamide compounds. In particular, the present invention relates to heterocyclic-substituted N-acetonylbenzamide compounds useful in controlling fungi. The compounds of the present invention are particularly useful in controlling phytopathogenic fungi.

There remains a need for effective fungicidal compounds. In a continuing attempt to provide new and effective fungicidal compounds, the compounds of the present invention were developed. The compounds of the present invention are N-acetonylbenzamides containing a heterocyclic ring fused to an aromatic ring. N-acetonylbenzamides are known in the art and are described in U.S. Pat. No. 4,822,902. It has been discovered that the compounds of the present invention, referred to herein as "heterocyclic N-acetonylbenzamides", are effective against phytopathogenic fungi, particularly fungi of the class Oomycetes.

According to a first aspect of the present invention there is provided a compound having the structural formula:

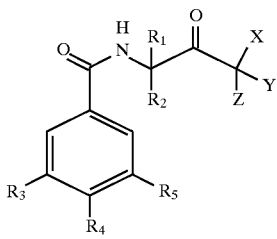

wherein:

$R_1$ and $R_2$ are independently selected from the group consisting of: H, $(C_1-C_6)$alkyl, $(C_1-C_6)$haloalkyl, $(C_2-C_6)$alkenyl, and $(C_2-C_6)$alkynyl; provided that at least one of $R_1$ and $R_2$ is not H;

$R_3$ is selected from the group consisting of: H, halo, cyano, $(C_1-C_6)$alkyl, $(C_1-C_6)$haloalkyl, $(C_2-C_6)$alkenyl, $(C_2-C_6)$alkynyl, $(C_1-C_6)$alkoxyl, $(C_1-C_6)$haloalkoxy, nitro, carboxyl, $NHCOOR_6$ $CR_6=NOR_7$, $CONR_8R_9$, and $NR_{10}R_{11}$;

$R_4$ and $R_5$ together form a fused 5, 6, or 7 membered carbocyclic ring containing at least one heteroatom selected from the group consisting of: O, S, N, and P;

$R_6$ is selected from the group consisting of: H, $(C_1-C_6)$ alkyl, $(C_2-C_6)$ alkenyl, and $(C_2-C_6)$ alkynyl;

$R_7$ is selected from the group consisting of: H, $(C_1-C_6)$ alkyl, $(C_2-C_6)$ alkenyl, and $(C_1-C_6)$ alkylcarbonyl;

$R_8$ and $R_9$ are independently selected from the group consisting of: H and $(C_1-C_6)$ alkyl;

$R_{10}$ and $R_{11}$ are each independently selected from the group consisting of: H, $(C_1-C_6)$ alkyl, and $(C_1-C_6)$ alkylcarbonyl; and X, Y, and Z are each independently selected from the group consisting of: H, halo, cyano, thiocyano, isothiocyano, and $(C_1-C_6)$alkylsulfonyloxy, provided that at least one of X, Y, and Z is selected from the group consisting of:, halo, cyano, thiocyano, isothiocyano, and $(C_1-C_6)$ alkylsulfonyloxy.

A second aspect of the present invention is a compound having the formula

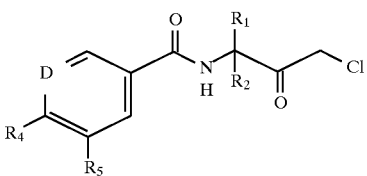

wherein:
D is selected from the group consisting of N and C—$R_3$;
$R_1$ and $R_2$ are independently selected from the group consisting of: H, $(C_1-C_6)$ alkyl, $(C_1-C_6)$ haloalkyl, $(C_2-C_6)$ alkenyl, and $(C_2-C_6)$ alkynyl; provided that at least one of $R_1$ and $R_2$ is not H;

$R_3$ is selected from the group consisting of: H, halo, cyano, $(C_1-C_6)$alkyl, $(C_1-C_6)$ haloalkyl, $(C_2-C_6)$alkenyl, $(C_2-C_6$ alkynyl, $(C_1-C_6)$alkoxyl, $(C_1-C_6)$haloalkoxy, nitro, carboxyl, $NHCOOR_6$, $CR_6=NOR_7$, $CONR_8R_9$ and $NR_{10}R_{11}$;

$R_4$ and $R_5$ together form a fused 5, 6, or 7 membered carbocyclic ring containing at least one heteroatom selected from the group consisting of: O, S, N, and P;

$R_6$ is selected from the group consisting of: H, $(C_1-C_6)$ alkyl, $(C_2-C_6)$ alkenyl, and $(C_2-C_6)$ alkynl;

$R_7$ is selected from the group consisting of: H, $(C_1-C_6)$ alkyl, $(C_2-C_6)$ alkenyl, and $(C_1-C_6)$ alkylcarbonyl;

$R_8$ and $R_9$ are independently selected from the group consisting of: H and $(C_1-C_6)$ alkyl;

$R_{10}$ and $R_{11}$ are each independently selected from the group consisting of: H, $(C_1-C_6)$ alkyl, and $(C_1-C_6)$ alkylcarbonyl; and X, Y, and Z are each independently selected from the group consisting of: H, halo, cyano, thiocyano, isothiocyano, and $(C_1-C_6)$alkylsulfonyloxy, provided that at least one of X, Y, and Z is selected from the group consisting of: halo, cyano, thiocyano, isothiocyano, and $(C_1-C_6)$ alkylsulfonyloxy.

Another aspect of the present invention is a compound having the formula:

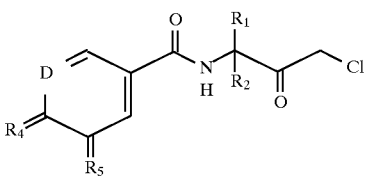

wherein:
D is selected from the group consisting of N and C—$R_3$;
$R_1$ and $R_2$ are independently selected from the group consisting of: H, $(C_1-C_6)$ alkyl, $(C_1-C_6)$ haloalkyl, $(C_2-C_6)$ alkenyl, and $(C_2-C_6)$ alkynyl; provided that at least one of $R_1$ and $R_2$ is not H;

$R_3$ is selected from the group consisting of: H, halo, cyano, $(C_1-C_6)$alkyl, $(C_1-C_6)$ haloalkyl, $(C_2-C_6)$alkenyl, $(C_2-C_6$ alkynyl, $(C_1-C_6)$alkoxyl, $(C_1-C_6)$haloalkoxy, nitro, carboxyl, $NHCOOR_6$, $CR_6=NOR_7$, $CONR_8R_9$ and $NR_{10}R_{11}$;

$R_4$ and $R_5$ together form a fused 5, 6, or 7 membered carbocyclic ring containing at least one heteroatom selected from the group consisting of: O, S, N, and P;

$R_6$ is selected from the group consisting of: H, $(C_1-C_6)$ alkyl, $(C_2-C_6)$ alkenyl, and $(C_2-C_6)$ alkynyl;

$R_7$ is selected from the group consisting of: H, $(C_1-C_6)$ alkyl, $(C_2-C_6)$ alkenyl, and $(C_1-C_6)$ alkylcarbonyl;

$R_8$ and $R_9$ are independently selected from the group consisting of: H and $(C_1-C_6)$ alkyl;

$R_{10}$ and $R_{11}$ are each independently selected from the group consisting of: H, $(C_1-C_6)$alkyl, and $(C_1-C_6)$ alkylcarbonyl; and X, Y, and Z are each independently selected from the group consisting of: H, halo, cyano, thiocyano, isothiocyano, and $(C_1-C_6)$alkylsulfonyloxy, provided that at least one of X, Y, and Z is selected from the group consisting of: halo, cyano, thiocyano, isothiocyano, and $(C_1-C_6)$ alkylsulfonyloxy.

Another aspect of the present invention is a compound having the formula:

[Chemical structure of pyridine derivative with substituents $R_3$, $R_4$, $R_5$, and amide group connected to $R_1$, $R_2$, and $CH_2Cl$]

wherein:

$R_1$ and $R_2$ are independently selected from the group consisting of: H, $(C_1-C_6)$ alkyl, $(C_1-C_6)$ haloalkyl, $(C_2-C_6)$ alkenyl, and $(C_2-C_6)$ alkynyl; provided that at least one of $R_1$ and $R_2$ is not H;

$R_3$ is selected from the group consisting of: H, halo, cyano, $(C_1-C_6)$alkyl, $(C_1-C_6)$ haloalkyl, $(C_2-C_6)$alkenyl, $(C_2-C_6$ alkynyl, $(C_1-C_6)$alkoxyl, $(C_1-C_6)$haloalkoxy, nitro, carboxyl, $NHCOOR_6$, $CR_6=NOR_7$, $CONR_8R_9$ and $NR_{10}R_{11}$;

$R_4$ and $R_5$ together form a fused 5, 6, or 7 membered carbocyclic ring containing at least one heteroatom selected from the group consisting of: O, S, N, and P;

$R_6$ is selected from the group consisting of: H, $(C_1-C_6)$ alkyl, $(C_2-C_6)$ alkenyl, and $(C_2-C_6)$ alkynl;

$R_7$ is selected from the group consisting of: H, $(C_1-C_6)$ alkyl, $(C_2-C_6)$ alkenyl, and $(C_1-C_6)$ alkylcarbonyl;

$R_8$ and $R_9$ are independently selected from the group consisting of: H and $(C_1-C_6)$ alkyl;

$R_{10}$ and $R_{11}$ are each independently selected from the group consisting of: H, $(C_1-C_6)$ alkyl, and $(C_1-C_6)$ alkylcarbonyl; and X, Y, and Z are each independently selected from the group consisting of: H, halo, cyano, thiocyano, isothiocyano, and $(C_1-C_6)$alkylsulfonyloxy, provided that at least one of X, Y, and Z is selected from the group consisting of: halo, cyano, thiocyano, isothiocyano, and $(C_1-C_6)$ alkylsulfonyloxy.

The present invention also includes the enantiomers, metal salts and complexes, and agronomically acceptable salts thereof.

The present invention also provides a method for control of phytopathogenic fungi comprising applying to the locus of a plant at least one of the above-described compounds.

As used herein, the term "alkyl" refers to straight carbon chains such as, for example, propyl, and to branched carbon chains such as, for example, in tert-butyl. Also included are cyclic carbon compounds containing up to 7 carbon atoms, such as, for example, cyclopropyl. "Alkenyl" refers to straight carbon chains containing a double bond. "Alkynl", as in, for example, "haloalkynyl", refers to straight carbon chains containing a triple bond. The term "$(C_1-C_6)$ alkylcarbonyl" refers to a straight or branched carbon chain containing a carbonyl group, such as, for example, $CH_3-CH_2-C(=O)$.

"Halo" is meant to include iodo, fluoro, bromo and chloro moieties.

Preferred compounds according to the method of the present invention are compounds having the structural formula above, wherein:

$R_1$ and $R_2$ are each independently selected from the group consisting of: $(C_1-C_6)$ alkyl;

$R_3$ is selected from the group consisting of: H, halo, cyano, $(C_1-C_6)$ alkyl, nitro, and $CR_6=NOR_7$;

$R_4$ and $R_5$ together form a fused 5, 6, or 7 membered carbocyclic ring containing at least one heteroatom selected from the group consisting of: O, S, N, and P;

$R_6$ is H;

$R_7$ is $(C_1-C_6)$ alkyl; and

X, Y, and Z are each independently selected from the group consisting of: H, halo, thiocyano, isothiocyano, and $(C_1-C_6)$ alkylsulfonyloxy, provided that at least one of X, Y, and Z is selected from the group consisting of: halo, thiocyano, isothiocyano, and $(C_1-C_6)$ alkylsulfonyloxy.

More preferred compounds according to the method of the present invention are compounds having the structural formula above, wherein:

$R_1$ and $R_2$ are each independently selected from the group consisting of $(C_1-C_3)$ alkyl;

$R_3$ is selected from the group consisting of: H, halo, cyano, $(C_1-C_6)$ alkyl, nitro, and $CR_6=NOR_7$;

$R_4$ and $R_5$ together form a fused 5, 6, or 7 membered carbocyclic ring containing at least one heteroatom selected from the group consisting of: O, S, N, and P;

$R_6$ is H;

$R_7$ is $CH_3$;

X, Y, and Z are each independently selected from the group consisting of: H, halo, thiocyano, isothiocyano, provided that at least two of X, Y, and Z are H.

Most preferred compounds according to the method of the present invention are compounds having the structural formula above, wherein:

$R_1$ is $CH_3$ and $R_2$ is $CH_2CH_3$;

$R_3$ is selected from the group consisting of: H, halo, cyano, $(C_1-C_6)$ alkyl, nitro, and $CR_6=NOR_7$;

$R_4$ and $R_5$ together form a fused 5, 6, or 7 membered carbocyclic ring containing at least one heteroatom selected from the group consisting of: O, S, N, and P;

$R_6$ is H;

$R_7$ is $CH_3$;

two of X, Y, and Z are H and one of X, Y, and Z is Cl.

The N-acetonylbenzamides (III) of the present invention may be prepared by reaction of the corresponding aromatic derivative (I) with α-amino-α'-chloroketone derivatives (II) as illustrated:

[Chemical scheme showing compound I (aromatic acid chloride with $R_3$, $R_4$, $R_5$ substituents and COCl group) reacting with compound II ($\alpha$-amino-$\alpha'$-chloroketone, $H_3N^+$ with $R_1$, $R_2$, and $CH_2Cl$, $Cl^-$)]

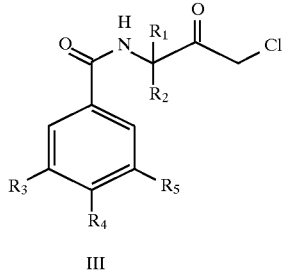

III where $R_4$ and $R_5$ together form a fused 5, 6, or 7 membered carbocyclic ring containing 1 or more heteroatoms such as O, S, N, or P. Optionally, the one or more heteroatoms may be in different oxidation states and bound to one or more additional heteroatoms as in a group such as, for example, $SO_n$, and $PO_n$ where n is 1 or 2.

Alternatively, compounds of structure III can be prepared by reaction of aromatic derivatives of structure I and α-amino-α', α'-dichloroketone derivatives of structure IIa, followed by selective removal of one chlorine atom. The removal of one chlorine atom may be accomplished, for example, by hydrogenation of the resulting dichloroketonebenzamide (IIIa) in the presence of a catalyst. Suitable catalysts include metals such as palladium or nickel. Palladium is the preferred metal catalyst. This alternative route is illustrated below:

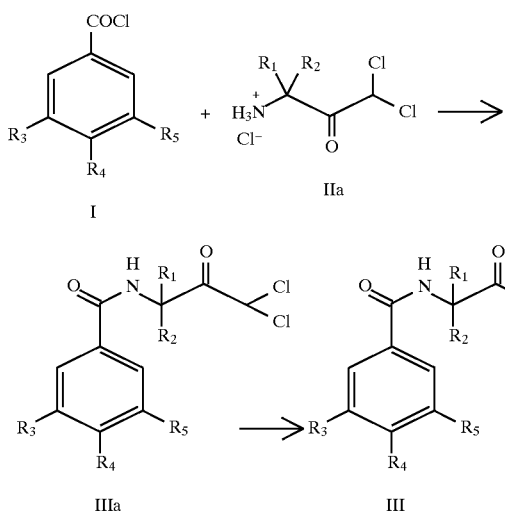

Compounds of formula II or IIa can be prepared by treating acetylenic amines (IV) with trifluoracetic anhydride in the presence of a solvent such as methylene chloride, chloroform, ethyl ether, or water and a base such as triethylamine, sodium carbonate, sodium bicarbonate, or sodium hydroxide to yield the acetylenic amide V:

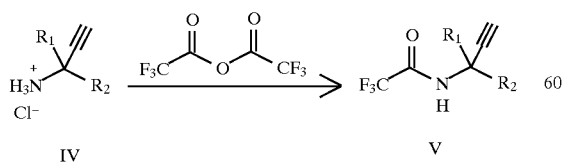

Treatment of the acetylenic amide V with chlorine or a chlorine source at a temperature of from −78° C. to 0° C. in the presence of a solvent such as methylene chloride or chloroform yields the intermediate oxazoline (VI). The oxazoline VI may be readily hydrolyzed under acidic conditions using an acid such as hydrochloric acid or sulfuric acid with a solvent such as methanol or tetrahydrofuran at a temperature of from 40° C. to 60° C., yielding the α-amino-α', α'-dichloroketone (IIa).

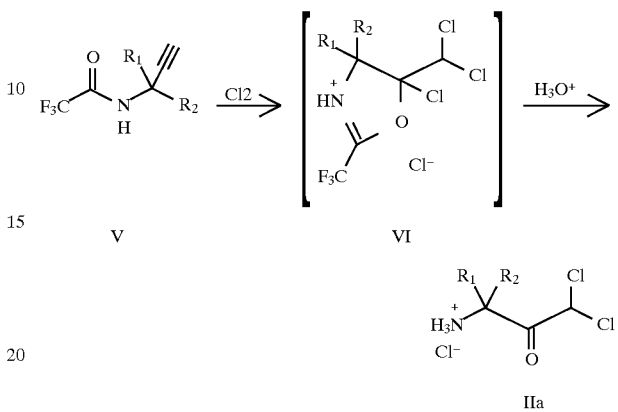

Selective catalytic dehalogenation of IIa yields the respective α-amino-α'-chloroketone II:

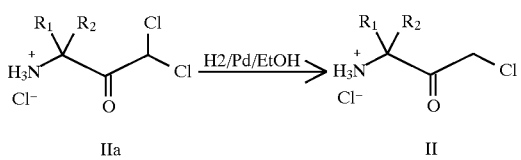

The aromatic portion of the heterocyclic acetonylbenzamides of the present invention may be prepared by methods known to those skilled in the art. For example, the 5-carboxybenzoxazole derivatives (VII and VIIa) may be prepared from the corresponding 2-aminophenol derivatives by procedures known in the art and described in, for example, E. C. Taylor, ed., *The Chemistry of Heterocyclic Compounds,* vol. 47,John Wiley & Sons, 1987 "Synthesis of Fused Heterocycles", edited by G. P. Ellis; p. 50, part I and pp. 713–714 part II). This procedure is set forth below:

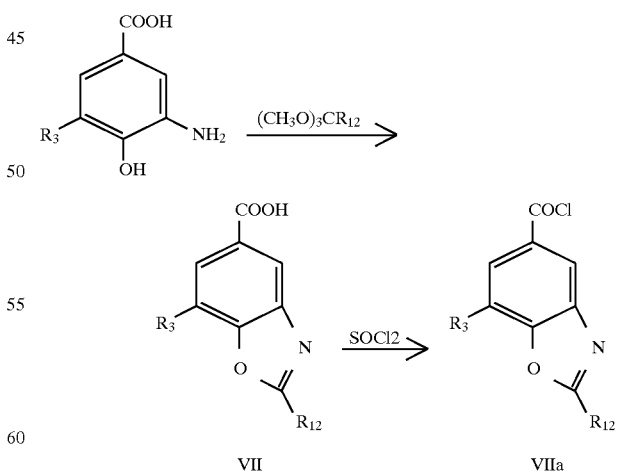

$R_3$ is selected from the group consisting of: H, halo, cyano, $(C_1-C_6)$alkyl, $(C_1-C_6)$ haloalkyl, $(C_2-C_6)$alkenyl, $(C_2-C_6$ alkynyl, $(C_1-C_6)$alkoxyl, $(C_1-C_6)$haloalkoxy, nitro, carboxyl, $NHCOOR_6$, $CR_6=NOR_7$, $CONR_8R_9$ and $NR_{10}R_{11}$;

$R_{12}$ is selected from the group consisting of: H, halo, cyano, $(C_1-C_6)$alkyl, $(C_1-C_6)$ haloalkyl, $(C_2-C_6)$alkenyl, $(C_2-C_6$ alkynyl, $(C_1-C_6)$alkoxyl, $(C_1-C_6)$haloalkoxy, nitro, carboxyl, $NHCOOR_6$, $CR_6=NOR_7$, $CONR_8R_9$ and $NR_{10}R_{11}$;

Similar procedures may be used to prepare the corresponding 6-carboxylbenzoxazole derivatives (Compounds VIII and VIIIa):

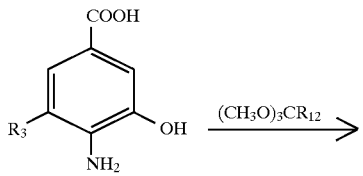

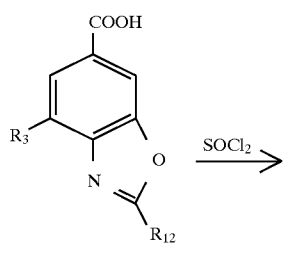 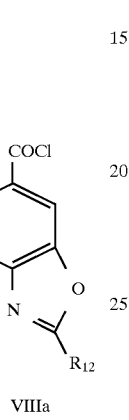

VIII                VIIIa

Similarly, 6-or 7- carboxy-1,4-benzoxazin-3-one derivatives may be prepared from the corresponding 2-aminophenol derivatives and chloroacetyl derivatives (Compounds IX and IXa). The procedures for the preparation of compounds such as IX and IXa, below, are described in, for example, *The Chemistry of Heterocyclic Compounds*, pp. 56–57.

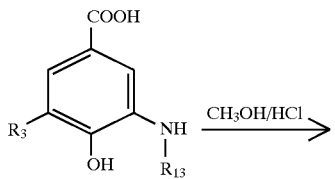

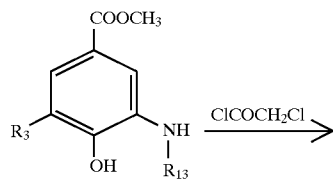

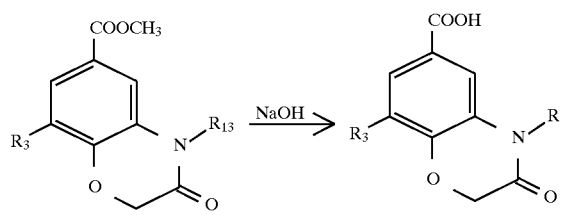

and                              IX

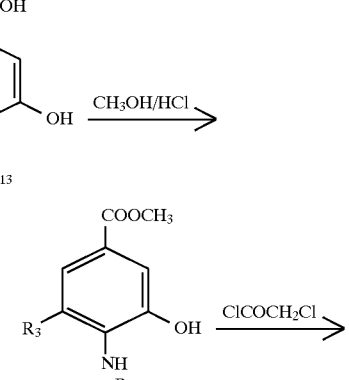

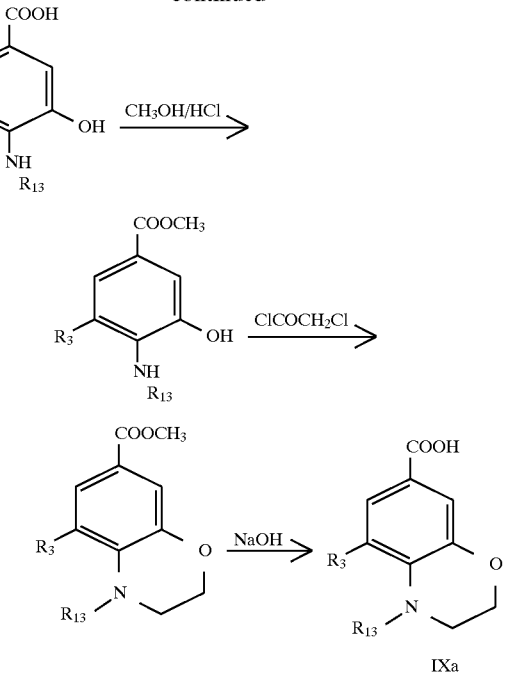

IXa $R_3$ is selected from the group consisting of: H, halo, cyano, $(C_1-C_6)$alkyl, $(C_1-C_6)$ haloalkyl, $(C_2-C_6)$alkenyl, $(C_2-C_6$ alkynyl, $(C_1-C_6)$alkoxyl, $(C_1-C_6)$haloalkoxy, nitro, carboxyl, $NHCOOR_6$, $CR_6=NOR_7$, $CONR_8R_9$ and $NR_{10}R_{11}$;

$R_{13}$ is selected from the group consisting of: H, halo, cyano, $(C_1-C_6)$alkyl, $(C_1-C_6)$ haloalkyl, $(C_2-C_6)$alkenyl, $(C_2-C_6$ alkynyl, $(C_1-C_6)$alkoxyl, $(C_1-C_6)$haloalkoxy, nitro, carboxyl, $NHCOOR_6$, $CR_6=NOR_7$, $CONR_8R_9$ and $NR_{10}R_{11}$;

and $R_6$, $R_7$, $R_8$, $R_9$, $R_{10}$, and $R_{11}$ are as defined hereinabove.

For example:

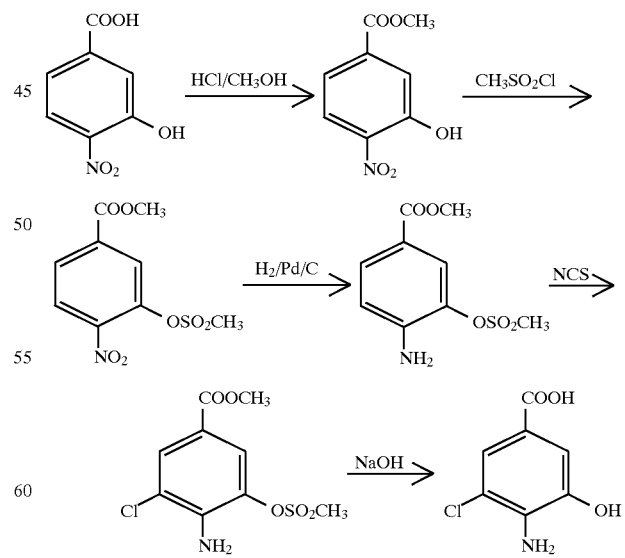

The intermediate compound X may be derivatized to form acyl chlorides XI and XII as indicated below:

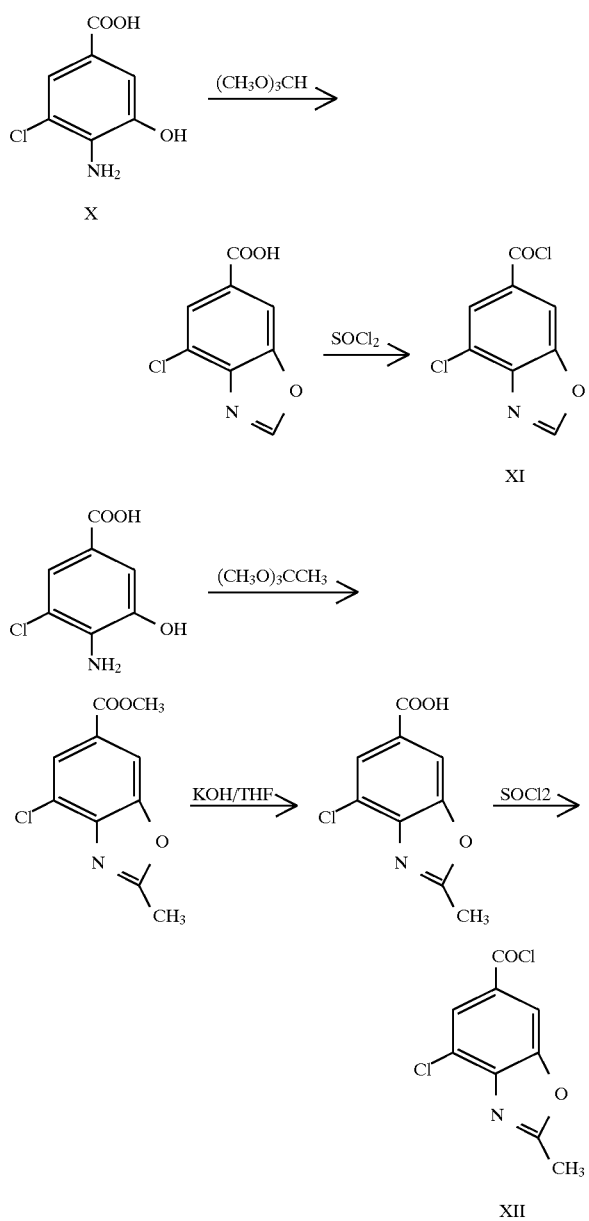

Alternatively, the following commercially available compounds (compounds XIIa, XIIb, and XIIc) may be used to make the aromatic portion of the heterocyclic N-acetonylbenzamides of the present invention:

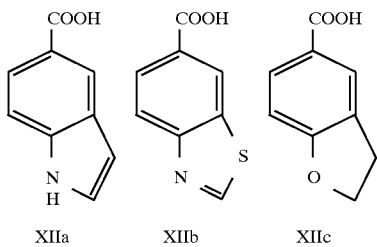

The compounds XIIa, XIIb, and XIIc are commercially available. Compound XIIa, indole-5-carboxylic acid, is available from Aldrich Chemicals (Catalog no. I-540-0). Compound XIIb, benzothiazole-6-carboxylic acid, is available from Maybridge Chemical Company Ltd. (Catalog no. KM 07305). Compound XIIc, 2,3-dihydrobenzo[B]furan-5-carboxylic acid, is available from Maybridge Chemical Company (Catalog no. 04-6766).

Starting materials in which the heterocyclic ring contains a P atom may be prepared according to known synthetic methods. For example, a compound containing a P atom may be prepared by the process fully described in: M. H. Beeby and F. G. Mann, *J. Chem. Soc.* 411 (1951).

Other methods by which a six membered ring containing a P atom may be prepared include: A. Couture, E. Deniau, and P. Grandclaudon, *J. Chem. Soc. Chem. Commun.* 11, 1329 (1994); G. Markl, G. Y. Yin, K. P. Berr, *Tetrahedron Letters* 34(19), p. 3102 (1993); and J. Kurita, T. Tsuchiya et al, *J. Chem. Soc., Chem. Commun.* 17, p. 1227 (1991). These starting materials may be used to form heterocyclic acetonylbenzamides according to the synthetic methods described herein.

The compounds of the present invention are useful as agricultural fungicides and, as such, can be applied to various loci of plants such as the seed, the growth medium, or the foliage. For such purposes these compounds may be used in the technical or pure form as prepared, or more typically as solutions or as formulations. The compounds are typically taken up in a carrier or are formulated so as to render them suitable for subsequent dissemination.

For use as fungicidal compounds, the compounds of the present invention may be applied according to conventional methods for the use of fungicides. The heterocyclic N-acetonylbenzamides may be applied separately, or may be combined to form a fungicidal composition before applying. As discussed herein, in most applications a fungicidal composition is used with an agronomically acceptable carrier. An "agronomically acceptable carrier" is a solid or liquid which is biologically, chemically, and physically compatible with the heterocyclic N-acetonylbenzamides of the present invention, and which may be used in agricultural applications. Agronomically acceptable carriers suitable for use in the method of the present invention include organic solvents and finely divided solids, both exemplified herein. For example fungicidal compositions can be formulated as wettable powders, emulsifiable concentrates, dusts, granular formulations, aerosols, or flowable emulsion concentrates. In such formulations, the fungicidal compounds are extended with a liquid or solid carrier and, when desired, suitable surfactants are incorporated.

Optional components, not required for fungicidal activity but useful or required for other properties, include, but are not limited to, adjuvants such as wetting agents, spreading agents, dispersing agents, stickers, adhesives and the like. Such adjuvants are well known in the art, and a discussion of adjuvants can be found in many references, such as in the John W. McCutcheon Inc. publication *McCutcheon's Emulsifiers and Detergents* (published annually by McCutcheon Division of MC Publishing Company, New Jersey). The compounds of the present invention may be used alone or in combination with other fungicides. Other fungicides suitable for use in combination with the compounds of the present invention include, but are not limited to, compounds listed in U.S. Pat. No. 5,304,572 beginning on line 30 of column 3 and continuing to line 52 of column 4. Other fungicides which may be used in combination with the compounds of the present invention include: acyclalanines such as furalaxyl, cyprofuram, ofurace, benalaxyl, and oxadixyl; fluazinam; flumetover; phenylbenzamide derivatives such as those disclosed in EP 578586 A1; amino acid derivatives such as valine derivatives disclosed in EP 550788 A1; methoxyacrylates such as methyl (E)-2-(2-(6-(2- cyanophenoxy)pyrimidin-4-yloxy)phenyl)-3-methoxyacrylate; benzo(1,2,3)thiadiazole-7-carbothioic acid S-methyl ester; propamocarb; imazalil; carbendazim; myclobutanil; fenbuconazole; tridemorph; pyrazophos; fenarimol; fenpiclonil; pyrimethanil; and tin fungicides. Those skilled in the art will recognize that mixtures of the compounds of the present invention with other fungicidally active compounds may provide advantages such as a broader spectrum of antifungal activity than the compounds of the present invention alone.

Similarly, the compounds of the present invention may be applied in combination with one or more insecticides such as those disclosed in U.S. Pat. No. 5,075,471 (columns 14 and 15). Those skilled in the art will recognize that mixtures of the compounds of the present invention with insecticidally active compounds may provide advantages such as fewer total applications than if the fungicides and insecticides are applied separately.

In order to obtain acceptable fungicidal activity by using the compounds and method of the present invention, a fungicidally effective amount of the N-acetonylbenzamides, or of a combination of the N-acetonylbenzamides with one or more other fungicides, must be used. As used herein, a "fungicidally effective amount" is a quantity of a compound which causes a reduction of fungal population or decreases crop damage as compared to a control group. A fungicidally effective amount of a particular compound for use against a particular fungus will depend upon the type of equipment employed, the method and frequency of application desired, and the diseases to be controlled, but is typically from about 0.01 to about 20 kilograms (kg) of active compound per hectare.

In general, the compounds of this invention may be dissolved in solvents such as acetone, methanol, ethanol, dimethylformamide, pyridine, or dimethyl sulfoxide, and such solutions may be diluted with water. The concentration of the solution after dilution may vary from 1% to 90% by weight, with a preferred range being from 5% to 50%.

For the preparation of emulsifiable concentrates of the compounds of the present invention, the compounds can be dissolved in a suitable organic solvent, or a mixture of solvents, together with an emulsifying agent to enhance dispersion of the compounds in water. The concentration of the total active ingredient in emulsifiable concentrates is usually from 10% to 90%, and in flowable emulsion concentrates can be as high as 75%. As used herein, the term "active ingredient" refers to the total amount of fungicide, including compounds of the present invention and any optional additional fungicide.

Wettable powders suitable for spraying can be prepared by admixing the fungicidal composition with a finely divided solid, such as clays, inorganic silicates and carbonates and silicas, and incorporating wetting agents, sticking agents and/or dispersing agents in such mixtures. The concentration of total active ingredients in such formulations is usually in the range of from 20% to 99% by weight, preferably from 40% to 75%. A typical wettable powder is made by blending 50 parts fungicide, 45 parts of a synthetic precipitated hydrated silicon dioxide, and 5 parts of sodium lignosulfonate. In another preparation a kaolin type clay is used in place of the hydrated silicon dioxide in the above wettable powder, and in another such preparation, 25% of the hydrated silicon dioxide is replaced with a synthetic sodium silicoaluminate sold under the trademark Zeolex®7 (J. M. Huber Corporation).

Dusts are prepared by mixing the fungicide with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from 20% to 80% of the active ingredient are commonly made and are subsequently diluted to from 1% to 10% concentration.

The fungicidal compounds may be applied as a fungicidal spray by methods commonly employed, such as conventional high-gallonage hydraulic sprays, low-gallonage sprays, air-blast sprays, aerial sprays and dusts. The dilution and rate of application will depend upon the type of equipment employed, the method of application, plants to be treated and diseases to be controlled. Generally, the compounds of the present invention will be applied in an amount of from 0.01 to 20 kilograms (kg) per hectare and preferably from 0.1 to 5 kg per hectare.

As a seed protectant, the fungicide may be coated on the seed. The usual dosage rate is from 0.05 ounce of active ingredient per hundred pounds of seed, to 20 ounces per hundred pounds of seed, preferably from 0.05 to 4 ounces per hundred pounds of seed. As a soil fungicide the fungicidal compounds may be incorporated into the soil or applied to the surface, usually at a rate of from 0.02 to 20, preferably from 0.05 to 10, and more preferably from 0.1 to 5 kg per hectare. As a foliar fungicide, the fungicidal compounds may be applied to growing plants at a rate of from 0.01 to 10 kg per hectare, preferably from 0.02 to 6 kg per hectare, and more preferably from 0.1 to 1.5 kg per hectare.

Exemplary compounds of the present invention are listed in Table 1.

TABLE 1

EXEMPLARY COMPOUNDS

| COMPOUND No. | $R_4R_5$ | $R_1$ | $R_2$ | $R_3$ | X | Y | Z |
| --- | --- | --- | --- | --- | --- | --- | --- |
| 1 | —N=CH—O— | —CH$_3$ | —CH$_2$CH$_3$ | H | Cl | H | H |
| 2 | —N=C(CH$_3$)—O— | —CH$_3$ | —CH$_2$CH$_3$ | H | Cl | H | H |
| 3 | —N=CH—O— | —CH$_3$ | —CH$_2$CH$_3$ | Cl | Cl | H | H |
| 4 | —N=CH—S— | —CH$_3$ | —CH$_2$CH$_3$ | H | Cl | H | H |
| 5 | —NH—CH=CH— | —CH$_3$ | —CH$_2$CH$_3$ | H | Cl | Cl | H |
| 6 | —NH—CH=CH— | —CH$_3$ | —CH$_2$CH$_3$ | H | Cl | H | H |
| 7 | —O—CH$_2$—CH$_2$— | —CH$_3$ | —CH$_2$CH$_3$ | H | Cl | Cl | H |
| 8 | —OCH=N— | —CH$_3$ | —CH$_2$CH$_3$ | H | Cl | H | H |
| 9 | —O—CH$_2$—CH$_2$— | —CH$_3$ | —CH$_2$CH$_3$ | H | Cl | H | H |

TABLE 1-continued

EXEMPLARY COMPOUNDS

| COMPOUND No. | $R_4R_5$ | $R_1$ | $R_2$ | $R_3$ | X | Y | Z |
|---|---|---|---|---|---|---|---|
| 10b | 70% —$CH_2$—$CH_2$—O— | —$CH_3$ | —$CH_2CH_3$ | H | Cl | H | H |
|  | 30% —CH=CH—O— | —$CH_3$ | —$CH_2CH_3$ | H | Cl | H | H |
| 11 | —O—$CH_2$—CO—NH | —$CH_3$ | —$CH_2CH_3$ | H | Cl | H | H |
| 12 | —N=C($CH_3$)—O— | —$CH_3$ | —$CH_2CH_3$ | Cl | Cl | H | H |
| 13 | —O—$CH_2$—CO—NH— | —$CH_3$ | —$CH_2CH_3$ | H | Cl | Cl | H |
| 14 | —N=C($CH_3$)—O— | —$CH_3$ | —$CH_2CH_3$ | H | Cl | Cl | H |
| 15 | —CH=CH—O— | —$CH_3$ | —$CH_2CH_3$ | H | Cl | Cl | H |

[a]R groups refer to structure III above.
[b]Compound No. 10 is a mixture, 70% of which is the compound in which $R_4R_5$ is —$CH_2$—$CH_2$—O— and 30% of which is the compound in which $R_4R_5$ is —CH=CH—O—.

The nuclear magnetic resonance data for the compounds made in the above examples is presented below.

TABLE 2

| EX # | Solvent | $H^1$-NMR Data (200 MHz, delta scale in ppm, Tetramethylsilane (TMS) standard*) |
|---|---|---|
| 1 | $CDCl_3$ | 8.25(1, s); 8.1(1, s); 7.8(1, d); 6.9(1, bs); 4.6–4.3(2, m); 2.3–1.9(2, m); 1.7(3, s); 0.9(3, t) |
| 2 | $CDCl_3$ | 8.0(1, s); 7.7(2, s); 6.9(1, bs); 4.6–4.3(2, m); 2.7)3, s); 2.4–1.8(2, m); 1.65(3, s); 0.9(3, t) |
| 3 | $CDCl_3$/ DMSO-d6 | 8.4(1, bs); 8.35(1, s); 8.2(1, s); 8.1(1, s); 4.5–4.3(2, m); 2.3–1.8(2, m); 1.55(3, s); 0.9(3, t) |
| 4 | $CDCl_3$ | 9.15(1, s); 8.5(1, s); 8.2(1, d); 7.9(1, d); 6.9(1, bs); 4.6–4.3(2, m); 2.3–1.8(2, m); 1.6(3, s); 0.8(3, t) |
| 5 | DMSO–d6 | 8.7(1, s); 8.25(1, s); 7.65(1, d) 7.5(1, s); 7.45(1, d); 6.95(1, s); 6.55(1, bs); 2.3–1.8(2, m) 1.5(3, s); 0.85(3, t) |
| 6 | DMSO–d6 | 8.65(1, bs); 8.25(1, s); 7.8–7.4(3, m); 6.55(1, bs); 4.5(2, s); 2.1–1.7(2, m); 1.45(3, s); 0.8(3, t) |
| 7 | $CDCl_3$/ DMSO-d6 | 7.75(1, s); 7.68(1, d); 7.35(1, bs); 6.85(1, d); 4.65(2, t); 4.6–4.3(2, m); 2.3–1.8(2, m); 1.55(3, s); 0.9(3, t) |
| 8 | $CDCl_3$ | 8.25(1, s); 8.20(1, s); 7.92(1, d); 7.67(1, d); 6.9(1, bs); 4.6–4.3(2, m); 2.3–1.8(2, m); 1.65(3, s); 0.9(3, t) |
| 9 | $CDCl_3$ | 7.7(2, s); 7.6(1, d); 6.8(1, d); 6.6(1, bs); 4.65(2, t); 4.6–4.3(2, m); 3.25(2, t); 2.3–1.8(2, m); 1.6(3, s); 0.85(3, t) |
| 10 | $CDCl_3$ | 8.1–6.5(m, aromatic protons); 4.65(t); 4.6–4.3(m); 2.2–1.8(m); 1.65(s); 0.9(t) |
| 11 | DMSO-d6 | 10.1(1, s); 7.55(1, d); 7.4(1, s); 7.05(1, d); 6.55(2, bs); 4.65(2, s); 4.55(2, s); 2.1–1.7(2, m); 1.35(3, s); 0.8(3, t) |
| 12 | $CDCl_3$ | 7.9(1, s) 7.75(1, s); 6.9(1, bs); 4.6–4.3(2, m); 2.75(3, s); 2.4–1.8(2, m); 1.65(3, s); 0.9(3, t) |
| 13 | DMSO-d6 | 8.75(1, bs); 7.6(1, d); 7.4(1, s); 7.05(2, d); 6.95(1, s); 4.65(2, s); 2.3–1.8(2m); 1.45(3, s); 0.85(3, t). |
| 14 | $CDCl_3$ | 8.6–7.6(3, m); 6.95(1, bs); 6.55(1, s); 2.65(3, s); 2.3–1.9(2m); 1.7(3, s); 0.95(3, t). |
| 15 | $CDCl_3$ | 8.4–7.7(4, m); 6.8(1, bs); 6.65(1, bs); 6.55(1, s); 2.3–1.9(2m); 1.7(3, s); 0.95(3, t). |

*bs: broad singlet; d: doublet, dd: double of doublets, t: triplet, q: quartet, m: multriplet, s: singlet.

EXAMPLES

The following examples are provided in order to illustrate the compounds and method of the present invention.

SYNTHESIS EXAMPLES

Examples 1 through 7 illustrate the synthesis methods used in making the intermediates described above and the exemplary compounds 1 through 15 listed in Table 1.

Example 1

Synthesis of Intermediates II and IIa

The preparation of these intermediates is illustrated by the synthesis of 3-amino-1-chloro-3-methyl-2-pentanone hydrochloride and 3-amino-1,1-dichloro-3-methyl-2-pentanone hydrochloride:

Synthesis of 3-Amino-1-chloro-3-methyl-2-pentanone hydrochloride and 3-Amino-1,1-dichloro-3-methyl-2-pentanone hydrochloride a) N-[3-(3-methyl-1-pentynyl)]trifluoroacetamide In a 3000 milliliter (ml) four-necked, round-bottomed flask fitted with a mechanical stirrer, nitrogen inlet, and thermometer a mixture was made of 234 grams (g) (1.75 mole) of 3-methyl-1-pentyn-3-amine hydrochloride and 1000 ml of methylene chloride. The mixture was stirred thoroughly and 354 g (3.51 mole) of triethylamine (TEA) were added dropwise, with the temperature maintained below 30° C. After the addition was completed the reaction mixture was stirred 120 minutes followed by dropwise addition of a solution containing 334.5 g (1.59 mole) of trifluoroacetic anhydride in 500 ml of methylene chloride. The addition was made at such a rate that the temperature was maintained at 0° C. After the addition was completed the reaction mixture was stirred at room temperature overnight and concentrated in vacuo. The resulting slurry was washed with ethyl ether. The ethyl ether layer was washed sequentially with water, saturated aqueous sodium bicarbonate and brine, dried over anhydrous magnesium sulfate, treated with activated charcoal, and filtered through a filter agent (Celite®, 95% $SiO_2$, from Aldrich Chemical Co., Milwaukee Wis.). The solvent was eliminated in a rotary evaporator. The resulting crude product was treated with cold pentane, filtered and dried, yielding 255.5 g (83%) of the expected N-[3-(3-methyl-1-pentynyl)]trifluoroacetamide as a white solid.

b) 2-trifluoromethyl-4-methyl-4-ethyl-5-chloro-5-(dichloromethyl) oxazoline hydrochloride In a 5 liter (1), four-necked, round-bottomed flask fitted with a mechanical stirrer, a thermometer and a gas inlet were dissolved 255.5 g (1.32 mole) of N-[3'-(3'-methyl-1'-pentynyl)]trifluoroacetamide in 4 l of methylene chloride. The resulting mixture was cooled down to −30° C. and 235 g of chlorine gas were bubbled into the mixture over a 2 hour period. When the addition was completed the reaction mixture was stirred at −30° C. for 30 minutes, then allowed to reach room temperature. The crude reaction mixture was evaporated in a rotary evaporator yielding the expected 2-trifluoromethyl-4-methyl-4-ethyl-5-chloro-5-(dichloromethyl)oxazoline hydrochloride which was used as such in the next step.

c) 3-Amino-1,1-dichloro-3-methyl-2-pentanone hydrochloride

The 2-trifluoromethyl-4-methyl-4-ethyl-5-chloro-5-(dichloromethyl)oxazoline hydrochloride prepared in the preceding step was dissolved in 1800 ml of methanol, 72 ml of water, and 190 ml of concentrated hydrochloric acid, warmed up to 50° C. and stirred at that temperature overnight. The crude reaction mixture was cooled down and poured into a mixture of ice/water/ethyl ether. The phases were separated and the ether layer was extracted once with water. The ether was saved (organic I). The combined aqueous layers were washed once with ethyl ether, and the organic layer was combined with organic I (organic II). The aqueous layer was neutralized with saturated aqueous sodium bicarbonate and extracted twice with ethyl ether. The combined ether layers were washed with water then brine, dried over anhydrous magnesium sulfate, treated with activated charcoal and filtered through Celite® filter agent. Anhydrous hydrogen chloride was bubbled into the filtrate while the temperature was maintained below 20° C. A white solid resulted. The white solid was filtered and dried yielding 124.8 g of the expected 3-amino-1,1-dichloro-3-methyl-2-pentanone hydrochloride as a white solid. The ethyl ether filtrate was combined with organic II and concentrated in vacuo The resulting residue (150 g) was taken up in a mixture of methanol/water/concentrated hydrochloric acid and heated at 50° C. for 72 hours. Filtration and drying as described above yielded another 51 g of 3-amino-1,1-dichloro-3-methyl-2-pentanone hydrochloride. The total amount obtained was 175.8 g (61%).

d) 3-Amino-1-chloro-3-methyl-2-pentanone hydrochloride

In a 2 1 Parr bottle were placed 41 g of 3-amino-1,1-dichloro-3-methyl-2-pentanone hydrochloride, 0.8 g of 10% palladium over charcoal and 400 ml of ethanol (200 proof). The resulting mixture was shaken in a Parr apparatus at 50 psi for 3 hours. The crude reaction mixture was filtered through Celite® filter agent and evaporated in vacuo. A viscous oil resulted, which was taken up in approximately 400 ml of ethyl acetate and stirred at room temperature for several hours. The expected 3-amino-1-chloro-3-methyl-2-pentanone hydrochloride crystallized as a white solid. To the resulting suspension were added 300 ml of hexane. Filtration yielded 34 g (98%) of the expected 3-amino-1-chloro-3-methyl-2-pentanone hydrochloride.

Example 2

Preparation of Compound 2 a) Methyl 2-methylbenzoxazole-6 carboxylate

In a 50 ml round-bottomed three-necked flask equipped with a 12-inch Vigraux column and a Dean Stark trap assembly were placed methyl 4-amino-3-hydroxybenzoate (10.0 g, 60 mmole), trimethylorthoacetate (10.8 g, 90 mmole), and concentrated sulfuric acid (0.25 g, 2.6 mmole). The resulting well-stirred mixture was heated at 115° C. until approximately 8 ml of methanol were collected in the Dean Stark trap. The reaction mixture was heated at 160° C. for another 60 minutes. The reaction mixture was cooled to room temperature and dissolved in ethyl acetate. The resulting organic solution was extracted sequentially with saturated aqueous sodium bicarbonate (1×100 ml), water (2×50 ml), brine, and dried over anhydrous magnesium sulfate. The solvent was removed in the rotary evaporator yielding 7.1 g of the expected methyl 2-methylbenzoxazole-6 carboxylate used as such in the next step.

b) 2-Methylbenzoxazole-6 carboxylic acid

In a 250 ml round-bottomed three-necked flask equipped with a reflux condenser were placed 5.1 g (26.7 mmole) methyl 2-methylbenzoxazole-6 carboxylate obtained by the previous step, 3.4 g (53.4 mmole) potassium hydroxide (pellets, 87%) and 160 ml methanol. The resulting mixture was stirred thoroughly, refluxed for 6 hours and stirred overnight at room temperature. The reaction mixture was concentrated in a rotary evaporator and taken up in a mixture of ethyl acetate and water. The ethyl acetate and water phases separated and the aqueous layer was washed with ethyl acetate (2×50 ml). The organic layers were discarded and the aqueous layer was acidified with concentrated hydrochloric acid and extracted several times with ethyl acetate. The combined organic layers were washed with water, dried over anhydrous magnesium sulfate and the solvent eliminated in a rotary evaporator yielding 2.3 g of the expected 2-methylbenzoxazole-6 carboxylic acid as a white solid. The product was used in the following step.

c) 2-Methylbenzoxazole-6 carboxyl chloride

In a 100 ml round-bottomed three-necked flask equipped with a reflux condenser were placed 0.9 g (5 millimoles (mmol) ) 2-methylbenzoxazole-6 carboxylic acid, 0.7 g (6 mmol) thionyl chloride, 2 drops dimethylformamide and 25 ml toluene. The resulting mixture was heated at 70° C. for 3 hours. The reaction mixture was cooled to room temperature. The solvent was removed in a rotary evaporator yielding the expected 2-methylbenzoxazole-6 carboxyl chloride as a thick oil. The product was used without further purification in the next step.

d) Compound 2

N-(3-chloro-1-ethyl-1-methyl-2-oxopropyl)-2-methylbenzoxazole-6-carboxamide

To a well-stirred mixture of 1.0 g (5.5 mmol) of compound II (R1=methyl, R2=ethyl) and 25 ml of methylene chloride in a 50 ml round-bottomed flask, placed in an ice bath, was added dropwise 1.5 g (15 mmol) triethylamine. After 15 minutes 1 g (5 mmol) 2-methylbenzoxazole-6 carboxyl chloride was added and methylene chloride (approximately 5 ml) was added dropwise. The mixture was stirred while the temperature was maintained at 0° C. to 5° C. for 2 hours. The reaction mixture was then poured into a mixture of ethyl acetate and water. The mixture separated into two phases, an organic phase and an aqueous phase. The organic phase was washed sequentially with saturated aqueous sodium bicarbonate (1×50 ml), water (1×50 ml), 2.5% aqueous hydrochloric acid (1×50 ml), and water (1×50 ml). The organic layer was dried over anhydrous magnesium sulfate and the solvent was removed in a rotary evaporator yielding the crude product. Chromatographic purification on a Silica Gel column (200–400 mesh, 60 Å, available from Aldrich Chemicals) with ethyl acetate:hexane (60:40) as elution solvent yielded 290 mg of the expected Compound 2 as a white solid.

Example 3

Preparation of intermediate XII a) Methyl 3-hydroxy-4-nitrobenzoate

In a 1 liter round-bottomed flask were placed 25 g (0.14 mole) 3-hydroxy-4-nitrobenzoic acid, 37% hydrochloric acid (37 ml) and methanol (300 ml). The resulting mixture was refluxed for 10 hours. The reaction mixture was cooled to room temperature and the solvent eliminated in a rotary evaporator. The resulting residue was dissolved in ethyl acetate and washed sequentially with water (1×100 ml), aqueous sodium bicarbonate (1×100 ml), water (1×100 ml) and brine (1×100 ml). The organic layer was dried over anhydrous magnesium sulfate and solvent was removed in the rotary evaporator, yielding 22.5 g of the expected methyl 3-hydroxy-4-nitrobenzoate as a yellow solid which was used as such in the next step.

b) Methyl 3-methylsulfonyloxy-4-nitrobenzoate

In a 1 liter round-bottomed flask were placed methyl 3-hydroxy-4-nitrobenzoate (21.7 g, 0.11 mole) and tetrahydrofuran (400 ml). To the resulting well-stirred mixture was added triethylamine (13.3 g, 0.132 mole) dropwise at −20° C. The reaction mixture was stirred at −20° C. for 10 minutes. Methanesulfonyl chloride (13.9 g, 0.121 mole) in methylene chloride (approximately 10 ml) was added slowly dropwise at such a rate as to keep the temperature at −20° C. After the addition was complete the reaction mixture was warmed up slowly to 0° C. and stirred at that temperature for 1 hour. The reaction mixture was poured into a mixture of water (500 ml) and ethyl ether (300 ml). The aqueous layer was separated and extracted with ethyl ether (2×300 ml). The combined ether layers were washed with water (2×250 ml), brine (1×250 ml) and dried over magnesium sulfate. The solvent was removed in the rotary evaporator and the resulting crude product triturated with hexane yielding 22.8 g of the expected methyl 3-methylsulfonyloxy-4-nitrobenzoate which was used as such in the next step.

c) Methyl 4-amino-3-methylsulfonyloxybenzoate

In a 2-liter Parr bottle were placed 10% palladium over charcoal (500 mg) and ethanol (200 proof; 50 ml). A mixture of 3-methylsulfonyloxy-4-nitrobenzoate (20 g, 72.7 mmole) and ethyl acetate (170 ml) was added followed by ethanol (350 ml). The bottle was placed in a Parr shaker apparatus, filled with hydrogen to 50 psi and shaken for 4.5 hours at that pressure. The reaction mixture was filtered through Celite® 545 and the solvent removed in the rotary evaporator yielding 18 g of the expected methyl 4-amino-3-methylsulfonylozybenzoate, which was used in the next step.

d) Methyl 4-amino-5-chloro-3-methylsulfonyloxybenzoate

In a 250 ml round-bottomed flask were placed methyl 4-amino-3-methylsulfonatebenzoate (8.5 g, 34.7 mmole) and acetonitrile (70 ml). The reaction mixture was warmed up to 50° C. and N-chlorosuccinimide (5.1 g, 38.2 mmole) was added. The resulting mixture was refluxed for 2 hours. The reaction mixture was cooled down to room temperature and the solvent eliminated in a rotary evaporator. The crude reaction product was partitioned between water and ethyl ether. The layers were separated, the organic layer was washed several times with water, dried over anhydrous magnesium sulfate and the solvent eliminated in the rotary evaporator until the mixture became a slurry, which was treated with hexane and filtered yielding 8.7 g of the expected methyl 4-amino-5-chloro-3-methylsulfonyloxybenzoate which was used as such in the next step.

e) 4-Amino-5-chloro-3-hydroxybenzoic acid

In a 2-liter round-bottomed flask were placed methyl 4-amino-5-chloro-3-methylsulfonyloxybenzoate (8.7 g, 31.1 mmole), 50% aqueous sodium hydroxide (10.1 g, 126 mmole), methanol (250 ml) and water (550 ml). The resulting mixture was refluxed for 3 hours. The reaction mixture was cooled down to room temperature and poured into a mixture of water and ethyl acetate. The aqueous layer was separated, neutralized to pH 6 with concentrated aqueous hydrochloric acid, and extracted with ethyl acetate (3×400 ml). The combined organic layers were washed with water (2×200 ml), dried over anhydrous magnesium sulfate and the solvent eliminated in the rotary evaporator yielding 4.3 g of the expected 4-amino-5-chloro-3-hydroxybenzoic acid (intermediate XII). ($^1$H-NMR, DMSO-$d_6$ 12.5(1,bs); 10(1,bs); 7.22(1,s); 5.4(2,s))

Example 4

Preparation of compounds 11 and 13 a) Preparation of methyl 1,4-benzoxazine-3-one-6-carboxylate

In a 250 ml three-necked round-bottomed flask were placed methyl 3-amino-4-hydroxybenzoate (5 g, 30 mmole), benzyltriethylammonium chloride (6.8 g, 30 mmole), chloroform (75 ml) and powdered sodium bicarbonate (10.1 g, 120 mmole). The resulting mixture was cooled down to 0° C. and a solution of chloroacetyl chloride (4.1 g, 36 mmole) in chloroform (20 ml) was added dropwise at such a rate as to keep the reaction temperature between 0° C. to 3° C. After the addition was complete the reaction mixture was stirred at 0° C. for another 90 minutes, followed by slow heating to 55° C., kept at that temperature for 8 hours, and finally stirred at room temperature overnight. The solvent was removed in a rotary evaporator, the resulting crude product was taken up in water, shaken and filtered yielding, after drying in a vacuum oven, 5.8 g of the expected methyl 1,4-benzoxazine-3-one-6-carboxylate which was used in the next step without further purification.

b) 1,4-benzoxazine-3-one-6-carboxylic acid

In a 250 ml round-bottomed flask were place the preceding methyl 1,4-benzoxazine-3-one-6-carboxylate (5.8 g, 28 mmole), 50% aqueous sodium hydroxide (9.0 g, 112 mmole), methanol (125 ml), and water (19 ml). The resulting mixture was refluxed for 4 hours. The reaction mixture was cooled to room temperature and the solvent eliminated in the rotary evaporator. The crude reaction product was taken up in water and the resulting aqueous solution was washed with hexane (2×50 ml) and acidified to pH=1 with concentrated aqueous hydrochloric acid. The solid which formed was separated by suction filtration, and dried in a vacuum oven yielding 5.1 g of the expected 1,4-benzoxazine-3-one-6-carboxylic acid.

Preparation of Compound 13 N-(3,3-dichloro-1-ethyl-1-methyl-2-oxopropyl)-1,4-benzoxazine-3-one-6-carboxamide In a 250 ml three-necked, round-bottomed flask fitted with a mechanical stirrer, nitrogen inlet and thermometer were placed 1.0 g (5.2 mmole) of 1,4-benzoxazine-3-one-6-carboxylic acid, 100 ml of tetrahydrofuran, 25 ml of dimethylformamide and 2.15 ml (15.5 mmole) of triethylamine. To the resulting well-stirred mixture was added 0.44 ml (5.72 mmole) of methane sulfonyl chloride dropwise while keeping the reaction temperature at −30° C. The resulting suspension was stirred at −30° C. for 15 minutes, after which 1.26 g (5.76 mmole) of 3-amino-1,1-dichloro-3-methyl-2-pentanone hydrochloride were added slowly over a 60 minute period. After the addition was completed, the reaction mixture was stirred at −30° C. for an additional 45 minutes. The reaction mixture was poured into a mixture of 100 ml of water and 50 ml of ethyl acetate. The phases were separated and the aqueous layer was extracted with ethyl acetate (3×50 ml). The combined organic phases were washed sequentially with water (1×75 ml), 3% aqueous hydrochloric acid (1×50 ml), brine (1×50 ml), saturated aqueous sodium bicarbonate (2×75 ml), and water (1×50 ml), and then dried over anhydrous magnesium sulfate. The solvent then was removed using a rotary evaporator, and the crude reaction product was purified by a short chromatography column (Silica Gel, eluted with methylene chloride followed by ethyl acetate) yielding 430 mg of a white solid (Compound 13).

Preparation of Compound 11 N-(3-chloro-1-ethyl-1-methyl-2-oxopropyl)-1,4-benzoxazine-3-one-6-carboxamide Compound 13 prepared in the previous step (210 mg), 30 ml of 200 proof ethanol, and 20 mg of 5% palladium over charcoal, were placed in a hydrogenation bottle and hydrogenated in a Parr apparatus (50 psi, at room temperature) for 3 hours. The reaction mixture was filtered through Celite® filtering agent and the solvent eliminated under reduced pressure in a rotary evaporator, to yield a crude product. The crude product was triturated with methanol and filtered yielding after drying 90 mg of the expected N-(3-chloro-1-ethyl-1-methyl-2-oxopropyl)-1,4-benzoxazine-3-one-6-carboxamide (compound 11).

Example 5

Preparation of Compounds 1, 3, 4, 8, and 12

Compounds 1, 3, 4, 8 and 12 were prepared using essentially the same procedure as for Compound 2.

Compound 1

6-Carboxy-1,3-benzoxazole was prepared from 4-amino-3-hydroxy benzoic acid by treatment with trimethylorthoformate. 6-Carboxy-1,3-benzoxazole was first treated with thionyl chloride to give the acid chloride. The acid chloride was treated with compound II (R1=CH3, R2=CH2CH3) in the presence of triethylamine to yield compound 1.

Compound 3

5-Carboxy-3-chloro-1,3-benzoxazole was prepared from 4-amino-5-chloro-3-hydroxy benzoic acid (compound X) by treatment with trimethylorthoformate. 5-Carboxy-3-chloro-1,3-benzoxazole was first treated with thionyl chloride to give the acid chloride. The acid chloride was treated with compound II (R1=CH3, R2=CH2CH3) in the presence of triethylamine to yield compound 3.

Compound 4

6-Carboxy-1,3-benzothiazole was purchased from Maybridge. 6-Carboxy-1,3-benzothiazole was first treated with thionyl chloride to give the acid chloride. The acid chloride was treated with compound II (R1=CH3, R2=CH2CH3) in the presence of triethylamine to yield compound 4.

Compound 8

5-Carboxy-1,3-benzoxazole was prepared from 3-amino-4-hydroxy benzoic acid by treatment with trimethylorthoformate. 5-Carboxy-1,3-benzoxazole was first treated with thionyl chloride to give the acid chloride. The acid chloride was treated with compound II (R1=CH3, R2=CH2CH3) in the presence of triethylamine to yield compound 8

Compound 12

5-Carboxy-2-methyl-3-chloro-1,3-benzoxazole was prepared from 4-amino-5-chloro-3-hydroxy benzoic acid (compound X) by treatment with trimethylorthoacetate. 5-Carboxy-2-methyl-3-chloro-1,3-benzoxazole was first treated with thionyl chloride to give the acid chloride. The acid chloride was treated with compound II (R1=CH3, R2=CH2CH3) in the presence of triethylamine to yield compound 12.

Example 6

Preparation of Compounds 6, 9, and 10

Compounds 6, 9 and 10 were prepared using essentially the same procedure as used for the preparation of Compound 11.

Compound 6

Compound 5 was treated with hydrogen in the presence of palladium over charcoal yielding compound 6.

Compound 9

Compound 6 was treated with hydrogen in the presence of palladium over charcoal yielding compound 9.

Compound 10

Compound 15 was treated with hydrogen in the presence of palladium over charcoal yielding compound 10. Compound 10 is a mixture of the corresponding benzofuran (30%) and 2,3-dihydrobenzofuran (70%) derivatives.

Example 7

Preparation of Compounds 5, 7, 13, and 14

Compound 5

5-Carboxy-indole was purchased from Aldrich. 5-Carboxy-indole was treated with methanesulfonyl chloride in the presence of triethylamine, followed by treatment with compound IIa (R1=CH3, R2=CH2CH3) in the presence of triethylamine to yield compound 5.

Compound 7

5-Carboxy-2,3-dihydrofuran was purchased from Maybridge. 5-Carboxy-2,3-dihydrofuran was treated with methanesulfonyl chloride in the presence of triethylamine, followed by treatment with compound IIa (R1=CH3, R2=CH2CH3) in the presence of triethylamine to yield compound 7.

Compound 14

6-Carboxy-2-methyl-1,3-benzoxazole was prepared from 4-amino-3-hydroxy benzoic acid by treatment with trimethylorthoacetate. 6-Carboxy-2-methyl-1,3-benzoxazole was first treated with thionyl chloride to give the acid chloride. The acid chloride was treated with compound IIa (R1=CH3, R2=CH2CH3) in the presence of triethylamine to yield compound 14.

Compound 15

6-Carboxy-benzofuran was prepared from methyl 4-formyl-3-hydroxy benzoate using the procedure of F. Duro and P. Condorelli *Ann. Chim.* (Roma) 53(11), 1582(1963). 6-Carboxy-benzofuran was treated with methanesulfonyl chloride in the presence of triethylamine, followed by treatment with compound IIa (R1=CH3, R2=CH2CH3) in the presence of triethylamine to yield compound 15.

Other compounds contemplated by this invention are listed in Tables 2, 3, 4 and 5. Compounds listed in Table 2 contain five-membered heterocyclic rings, and compounds listed in Table 3 contain six-membered or seven-membered heterocyclic rings. In Tables 2 and 3 the R-groups refer to the structure:

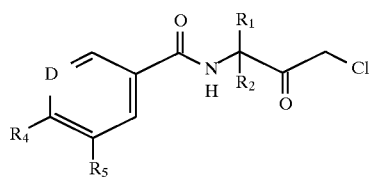

TABLE 2

Representative Compounds Containing Five-membered Heterocyclic Rings

| No. | $R_1$ | $R_2$ | D | $R_4R_5$ |
|---|---|---|---|---|
| 1 | $CH_3-$ | $CH_3CH_2-$ | N | $-N(CH_3)-CH=N-$ |
| 2 | $CH_3-$ | $CH_3CH_2-$ | N | $-N=CH-N(CH_3)-$ |
| 3 | $CH_3-$ | $CH_3CH_2-$ | N | $-CH=CH-O-$ |
| 4 | $CH_3-$ | $CH_3CH_2-$ | N | $-CH=CH-S-$ |
| 5 | $CH_3-$ | $CH_3CH_2-$ | N | $-CH=CH-NH-$ |
| 6 | $CH_3-$ | $CH_3CH_2-$ | N | $-CH=CH-N(CH_3)$ |
| 7 | $CH_3-$ | $CH_3CH_2-$ | N | $-N=CH-O-$ |
| 8 | $CH_3-$ | $CH_3$ | N | $-N=CH-O-$ |
| 9 | $CH_3-$ | $CH_3CH_2-$ | N | $-N=CH-S-$ |
| 10 | $CH_3-$ | $CH_3-$ | N | $-N=CH-S-$ |
| 11 | $CH_3-$ | $CH_3CH_2-$ | C—Cl | $-CH=CH-O-$ |
| 12 | $CH_3-$ | $CH_3CH_2-$ | C—Cl | $-CH=CH-S-$ |
| 13 | $CH_3-$ | $CH_3CH_2-$ | N | $-O-CH=CH-$ |
| 14 | $CH_3-$ | $CH_3CH_2-$ | N | $-S-CH=CH-$ |
| 15 | $CH_3-$ | $CH_3CH_2-$ | N | $-NH-CH=CH-$ |
| 16 | $CH_3-$ | $CH_3CH_2-$ | N | $-N(CH_3)-CH=CH-$ |
| 17 | $CH_3-$ | $CH_3CH_2-$ | C—CN | $-O-CH=CH-$ |
| 18 | $CH_3-$ | $CH_3CH_2-$ | C—CN | $-S-CH=CH-$ |
| 19 | $CH_3-$ | $CH_3CH_2-$ | C—CN | $-NH-CH=CH-$ |
| 20 | $CH_3-$ | $CH_3CH_2-$ | C—CN | $-N(CH_3)-CH=CH-$ |
| 21 | $CH_3-$ | $CH_3CH_2-$ | $C-CH=NOCH_3$ | $-O-CH=CH-$ |
| 22 | $CH_3-$ | $CH_3CH_2-$ | $C-CH=NOCH_3$ | $-S-CH=CH-$ |
| 23 | $CH_3-$ | $CH_3CH_2-$ | $C-CH=NOCH_3$ | $-NH-CH=CH-$ |
| 24 | $CH_3-$ | $CH_3CH_2-$ | $C-CH=NOCH_3$ | $-N(CH_3)-CH=CH-$ |
| 25 | $CH_3-$ | $CH_3$ | C—CN | $-O-CH=CH-$ |
| 26 | $CH_3-$ | $CH_3$ | C—CN | $-S-CH=CH-$ |
| 27 | $CH_3-$ | $CH_3$ | C—CN | $-NH-CH=CH-$ |
| 28 | $CH_3-$ | $CH_3$ | C—CN | $-N(CH_3)-CH=CH-$ |
| 29 | $CH_3-$ | $CH_3$ | $C-CH=NOCH_3$ | $-O-CH=CH-$ |
| 30 | $CH_3-$ | $CH_3$ | $C-CH=NOCH_3$ | $-S-CH=CH-$ |
| 31 | $CH_3-$ | $CH_3$ | $C-CH=NOCH_3$ | $-NH-CH=CH-$ |
| 32 | $CH_3-$ | $CH_3$ | $C-CH=NOCH_3$ | $-N(CH_3)-CH=CH-$ |
| 33 | $CH_3-$ | $CH_2CH_3$ | C—Cl | $-O-CH=CH-$ |
| 34 | $CH_3-$ | $CH_2CH_3$ | C—Cl | $-S-CH=CH-$ |
| 35 | $CH_3-$ | $CH_2CH_3$ | C—Cl | $-N(CH_3)-CH=CH-$ |
| 36 | $CH_3-$ | $CH_2CH_3$ | C—Cl | $-CH=N-O-$ |
| 37 | $CH_3-$ | $CH_2CH_3$ | C—Cl | $-CH=N-S-$ |
| 38 | $CH_3-$ | $CH_2CH_3$ | C—Cl | $-CH=N-NH-$ |
| 39 | $CH_3-$ | $CH_2CH_3$ | C—Cl | $-CH=N-N(CH_3)-$ |
| 40 | $CH_3-$ | $CH_2CH_3$ | C—Cl | $-N=CH-O-$ |
| 41 | $CH_3-$ | $CH_2CH_3$ | C—Cl | $-N=CH-S-$ |
| 42 | $CH_3-$ | $CH_2CH_3$ | N | $-CH=N-O-$ |
| 43 | $CH_3-$ | $CH_2CH_3$ | N | $-CH=N-S-$ |
| 44 | $CH_3-$ | $CH_2CH_3$ | N | $-CH=N-NH-$ |
| 45 | $CH_3-$ | $CH_2CH_3$ | N | $-CH=N-N(CH_3)-$ |
| 46 | $CH_3-$ | $CH_2CH_3$ | C—Cl | $-O-N=CH-$ |
| 47 | $CH_3-$ | $CH_2CH_3$ | C—Cl | $-S-N=CH-$ |
| 48 | $CH_3-$ | $CH_2CH_3$ | C—Cl | $-NH-N=CH-$ |
| 49 | $CH_3-$ | $CH_2CH_3$ | C—Cl | $-N(CH_3)-N-CH-$ |
| 50 | $CH_3-$ | $CH_2CH_3$ | N | $-N(CH_3)-CO-O-$ |
| 51 | $CH_3-$ | $CH_2CH_3$ | N | $-N(CH_3)-CO-S-$ |
| 52 | $CH_3-$ | $CH_2CH_3$ | N | $-N(CH_3)-CO-N(CH_3)-$ |
| 53 | $CH_3-$ | $CH_2CH_3$ | N | $-O-CO-N(CH_3)-$ |
| 54 | $CH_3-$ | $CH_2CH_3$ | N | $-S-CO-N(CH_3)-$ |
| 55 | $CH_3-$ | $CH_2CH_3$ | C—Cl | $-N(CH_3)-CO-O-$ |
| 56 | $CH_3-$ | $CH_2CH_3$ | C—Cl | $-N(CH_3)-CO-S-$ |
| 57 | $CH_3-$ | $CH_2CH_3$ | C—Cl | $-N(CH_3)-CO-N(CH_3)-$ |
| 58 | $CH_3-$ | $CH_2CH_3$ | C—Cl | $-O-CO-N(CH_3)-$ |
| 59 | $CH_3-$ | $CH_2CH_3$ | C—Cl | $-S-CO-N(CH_3)$ |
| 60 | $CH_3-$ | $CH_2CH_3$ | C—Cl | $-S-CH=N-$ |
| 61 | $CH_3-$ | $CH_2CH_3$ | C—Cl | $-S-CH=N-$ |
| 62 | $CH_3-$ | $CH_2CH_3$ | C—Cl | $-O-CH=N-$ |
| 63 | $CH_3-$ | $CH_2CH_3$ | N | $-S-CH=N-$ |
| 64 | $CH_3-$ | $CH_2CH_3$ | N | $-O-CH=N-$ |
| 65 | $CH_3-$ | $CH_3$ | C—Cl | $-S-CH=N-$ |
| 66 | $CH_3-$ | $CH_3$ | C—Cl | $-O-CH=N-$ |
| 67 | $CH_3-$ | $CH_3$ | N | $-S-CH=N-$ |
| 68 | $CH_3-$ | $CH_3$ | N | $-O-CH=N-$ |

TABLE 3

Representative Compounds Containing Six-membered or Seven-membered Heterocyclic Rings

| No. | R₁ | R₂ | D | R₄R₅ |
|---|---|---|---|---|
| 69 | CH₃— | CH₃CH₂— | N | —N(CH₃)—CO—CH₂—O— |
| 70 | CH₃— | CH₃CH₂— | N | —N(CH₃)—CO—CH₂—S— |
| 71 | CH₃— | CH₃CH₂— | N | —N(CH₃)—CO—CH₂—N(CH₃)— |
| 72 | CH₃— | CH₃CH₂— | N | —O—CH₂—CO—N(CH₃)— |
| 73 | CH₃— | CH₃CH₂— | N | —S—CH₂—CO—N(CH₃)— |
| 74 | CH₃— | CH₃CH₂— | N | —N(CH₃)—CH₂—CO—N(CH₃)— |
| 75 | CH₃— | CH₃CH₂— | C—Cl | —N(CH₃)—CO—CH₂—O— |
| 76 | CH₃— | CH₃CH₂— | C—Cl | —N(CH₃)—CO—CH₂—S— |
| 77 | CH₃— | CH₃CH₂— | C—Cl | —N(CH₃)—CO—CH₂—N(CH₃)— |
| 78 | CH₃— | CH₃CH₂— | C—Cl | —O—CH₂—CO—N(CH₃)— |
| 79 | CH₃— | CH₃CH₂— | C—Cl | —S—CH₂—CO—N(CH₃)— |
| 80 | CH₃— | CH₃CH₂— | C—Cl | —N(CH₃)—CH₂—CO—N(CH₃)— |
| 81 | CH₃— | CH₃CH₂— | N | —N(CH₃)—CH=CH—O— |
| 82 | CH₃— | CH₃CH₂— | N | —N(CH₃)—CH=CH—S— |
| 83 | CH₃— | CH₃CH₂— | N | —N(CH₃)—CH=CH—N(CH₃)— |
| 84 | CH₃— | CH₃CH₂— | N | —O—CH=CH—N(CH₃)— |
| 85 | CH₃— | CH₃CH₂— | N | —S—CH=CH—N(CH₃)— |
| 86 | CH₃— | CH₃CH₂— | C—Cl | —N(CH₃)—CH=CH—O— |
| 87 | CH₃— | CH₃CH₂— | C—Cl | —N(CH₃)—CH=CH—S— |
| 88 | CH₃— | CH₃CH₂— | C—Cl | —N(CH₃)—CH=CH—N(CH₃)— |
| 89 | CH₃— | CH₃CH₂— | C—Cl | —O—CH=CH—N(CH₃)— |
| 90 | CH₃— | CH₃CH₂— | C—Cl | —S—CH=CH—N(CH₃)— |
| 91 | CH₃— | CH₃CH₂— | N | —CO—CH=CH—N(CH₃)— |
| 92 | CH₃— | CH₃CH₂— | N | —CO—CH=CH—O— |
| 93 | CH₃— | CH₃CH₂— | N | —CO—CH=CH—S— |
| 94 | CH₃— | CH₃CH₂— | N | —N(CH₃)—CH=CH—CO— |
| 95 | CH₃— | CH₃CH₂— | N | —O—CH=CH—CO— |
| 96 | CH₃— | CH₃CH₂— | N | —S—CH=CH—CO— |
| 97 | CH₃— | CH₃CH₂— | C—Cl | —CO—CH=CH—N(CH₃)— |
| 100 | CH₃— | CH₃CH₂— | C—Cl | —CO—CH=CH—O— |
| 101 | CH₃— | CH₃CH₂— | C—Cl | —CO—CH=CH—S— |
| 102 | CH₃— | CH₃CH₂— | C—Cl | —N(CH₃)—CH=CH—CO— |
| 103 | CH₃— | CH₃CH₂— | C—Cl | —O—CH=CH—CO— |
| 104 | CH₃— | CH₃CH₂— | C—Cl | —S—CH=CH—CO— |
| 105 | CH₃— | CH₃CH₂— | C—CN | —CO—CH=CH—O— |
| 106 | CH₃— | CH₃CH₂— | C—CN | —CO—CH=CH—S— |
| 107 | CH₃— | CH₃CH₂— | C—CN | —N(CH₃)—CH=CH—CO— |
| 108 | CH₃— | CH₃CH₂— | C—CN | —O—CH=CH—CO— |
| 109 | CH₃— | CH₃CH₂— | C—CN | —S—CH=CH—CO— |
| 110 | CH₃— | CH₃CH₂— | C—CH=NOCH₃ | —CO—CH=CH—O— |
| 111 | CH₃— | CH₃CH₂— | C—CH=NOCH₃ | —CO—CH=CH—S— |
| 112 | CH₃— | CH₃CH₂— | C—CH=NOCH₃ | —N(CH₃)—CH=CH—CO— |
| 113 | CH₃— | CH₃CH₂— | C—CH=NOCH₃ | —O—CH=CH—CO— |
| 114 | CH₃— | CH₃CH₂— | C—CH=NOCH₃ | —S—CH=CH—CO— |
| 115 | CH₃— | CH₃CH₂— | N | —N=CH—CH=CH—O— |
| 116 | CH₃— | CH₃CH₂— | N | —O—CH=CH—CH=N— |
| 117 | CH₃— | CH₃CH₂— | C—Cl | —N=CH—CH=CH—O— |
| 118 | CH₃— | CH₃CH₂— | C—Cl | —O—CH=CH—CH=N— |
| 119 | CH₃— | CH₃CH₂— | C—Cl | —P(CH₃)—(CH₂)₃— |

TABLE 4

Compounds listed in Table 4 refer to the structure:

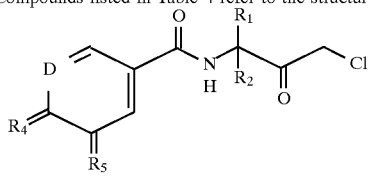

| No. | R₁ | R₂ | D | R₄R₅ |
|---|---|---|---|---|
| 120 | CH₃— | CH₃CH₂— | N | =N—CH=N—CH= |
| 121 | CH₃— | CH₃CH₂— | N | =CH—N=CH—N= |
| 122 | CH₃— | CH₃CH₂— | N | =N—CO—N(CH₃)—CH= |
| 123 | CH₃— | CH₃CH₂— | N | =CH—N(CH₃)—CO—N= |
| 124 | CH₃— | CH₃CH₂— | C—Cl | =N—CH=N—CH= |
| 125 | CH₃— | CH₃CH₂— | C—Cl | =CH—N=CH—N= |
| 126 | CH₃— | CH₃CH₂— | C—Cl | =N—CO—N(CH₃)—CH= |
| 127 | CH₃— | CH₃CH₂— | C—Cl | =CH—N(CH₃)—CO—N= |

TABLE 4-continued

Compounds listed in Table 4 refer to the structure:

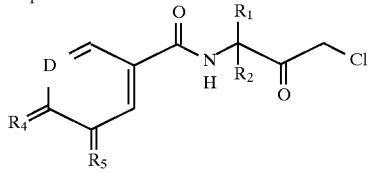

| No. | R₁ | R₂ | D | R₄R₅ |
|---|---|---|---|---|
| 128 | CH₃— | CH₃CH₂— | C—Cl | =N—CH=CH—N= |
| 129 | CH₃— | CH₃CH₂— | C—CHN=OCH₃ | =N—CH=CH—N= |
| 130 | CH₃— | CH₃CH₂— | C—CN | =N—CH=CH—N= |

TABLE 5

Compounds in Table 5 refer to the following structure:

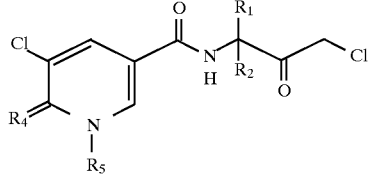

| No. | R₁ | R₂ | R₃ | R₄R₅ |
|---|---|---|---|---|
| 131 | CH₃— | CH₃CH₂— | Cl | =N—CH=CH— |
| 132 | CH₃— | CH₃CH₂— | Cl | =N—CH₂—CO— |
| 133 | CH₃— | CH₃CH₂— | Cl | =N—CO—CH₂— |
| 134 | CH₃— | CH₃CH₂— | Cl | =N—CH₂—CH₂— |
| 135 | CH₃— | CH₃CH₂— | C—CN | =N—CH=CH— |
| 136 | CH₃— | CH₃CH₂— | C—CN | =N—CH₂—CO— |
| 137 | CH₃— | CH₃CH₂— | C—CN | =N—CO—CH₂— |
| 138 | CH₃— | CH₃CH₂— | C—CN | =N—CH₂—CH₂— |
| 139 | CH₃— | CH₃CH₂— | CH=NOCH₃ | =N—CH=CH— |
| 140 | CH₃— | CH₃CH₂— | CH=NOCH₃ | =N—CH₂—CO— |
| 141 | CH₃— | CH₃CH₂— | CH=NOCH₃ | =N—CO—CH₂— |
| 142 | CH₃— | CH₃CH₂— | CH=NOCH₃ | =N—CH₂—CH₂— |

Examples 8 and 9

Fungicidal Activity

Examples 8 and 9 illustrate the testing for fungicidal activity of the compounds of the present invention.

Example 8

Fungitoxicity against *Pythium ultimum*

Compounds were tested for fungitoxicity against *Pythium ultimum* according to the procedures set forth below. Results are presented in Table 6.

Test compounds were dissolved in dimethylsulfoxide at 20 mg/ml and 0.1 ml was added to 19.9 ml of a liquid asparagine-sucrose broth, prepared according to the method described in Erwin, D. C., and Katznelson, K., *Canadian Journal of Microbiology* 7, 15 (1971), in 9 cm petri dishes to give a concentration of 100 ppm of the compound. Each plate was inoculated with a mycelial plug, 7 mm in diameter, taken from the growing edge of a culture of *Pythium ultimum* grown on potato dextrose agar. Two replicate plates were used for each treatment. After growth for 48 hours at 25° C. with shaking on a gyrotary shaker at 60 rpm, the increase in mycelial dry weight was determined. Fungitoxicity was recorded as percent inhibition of growth as compared to controls lacking the test compounds. Results are presented in Table 2.

TABLE 6

Fungitoxicity of test compounds against *Pythium ultimum*

| Compound | % Inhibition |
|---|---|
| 1 | 89.4 |
| 2 | 92.2 |
| 3 | 92.0 |
| 4 | 94.2 |
| 5 | 66.9 |
| 6 | 88.6 |
| 7 | 94.5 |
| 8 | 93.7 |
| 9 | 91.6 |
| 10 | 91.0 |
| 11 | 34.3 |
| 12 | 90.7 |
| 13 | 60.8 |
| 14 | 94.5 |

Example 9

Fungitoxicity against *Phytophthora infestans*, *Plasmopara viticola*, and *Pseudoperonospora cubensis*

Compounds were tested for fungicidal activity against fungal diseases caused by *Phytophthora infestans* (tomato late blight), *Plasmopara viticola* (grape downy mildew), and *Pseudoperonospora cubensis* (cucumber downy mildew) according to the procedures set forth below. Results are presented in Table 7.

Tomato Late Blight (TLB)

Spore suspensions, obtained from 1–2 week old *Phytophthora infestans* cultures grown on V8® juice agar, were used to inoculate tomato seedlings that were about two weeks old. An atomizer was used to apply the spores to the fungicide-treated foliage. The plants were kept in a humidity cabinet at 100% humidity for 24 hours, and then placed in a controlled temperature chamber at 20° C. for disease development. Disease evaluations were made 6 days after inoculation and were recorded as "percent disease control", i.e., the relative efficacy of the test compound compared to no treatment, with 100% disease control indicating that the plants were observed to be disease free.

V8® is registered trademark of Campbell Soup Co.)

Grape Downy Mildew (GDM)

Cultures of *Plasmopara viticola* were maintained on grape seedlings derived from tissue culture. Leaves with sporulating mildew were rinsed in water to obtain a spore suspension. An atomizer was used to apply the suspension of spores to the lower leaves of the grape plants. The plants were kept in a humidity cabinet at 100% humidity for 24 hours and then placed in a controlled temperature chamber at 20° C. for 7–8 days for disease development. Disease evaluations were recorded as percent disease control, according to the method described above for tomato late blight.

Cucumber Downy Mildew

Cultures of *Pseudoperonospora cubensis* were maintained on Bush Champion cucumbers. Spore suspensions were obtained by washing spores from infected leaves. An atomizer was used to apply a suspension of spores to the lower leaves of the cucumbers. Following inoculation, the plants were kept in a humidity cabinet at 100% humidity for 24 hours and then placed in a controlled temperature chamber at 20° C. Disease evaluations were made 7 days after inoculation and were recorded as percent disease control, according to the method described above for tomato late blight.

TABLE 7

EFFECTIVENESS OF
TEST COMPOUNDS AGAINST FUNGAL DISEASES

| COMPOUND | Rate (ppm) | TLB | GDM | CDM |
|---|---|---|---|---|
| 1 | 375 | 100 | — | — |
| 2 | 300 | 90 | 100 | — |
| 3 | 300 | 100 | 100 | — |
| 4 | 300 | 100 | — | 50 |
| 5 | 750 | 0 | — | 50 |
| 6 | 300 | 100 | 100 | — |
| 7 | 300 | 300 | — | — |
| 8 | 300 | 90 | 100 | — |
| 9 | 300 | 100 | 0 | — |
| 10 | 300 | 85 | 0 | — |
| 11 | 300 | 95 | 0 | — |
| 12 | 300 | 95 | 90 | — |

What is claimed is:

1. A compound having the formula:

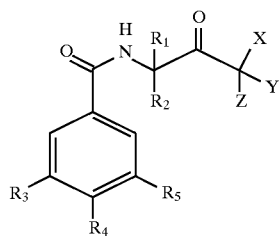

wherein:
- $R_1$ is selected from the group consisting of: H, $(C_1-C_6)$ alkyl, $(C_1-C_6)$ haloalkyl, $(C_2-C_6)$ alkenyl, and $(C_2-C_6)$ alkynyl;
- $R_2$ is selected from the group consisting of: $(C_1-C_6)$ alkyl, $(C_1-C_6)$ haloalkyl, $(C_1-C_6)$ alkenyl, and $(C_2-C_6)$ alkynyl;
- $R_3$ is selected from the group consisting of: H, halo, cyano, $(C_1-C_6)$ alkyl, $(C_1-C_6)$ haloalkyl, $(C_2-C_6)$ alkenyl, $(C_2-C_6)$ alkynyl, $(C_1-C_6)$ alkoxy, $(C_1-C_6)$ haloalkoxy, nitro, carboxyl, $NHCOOR_6$, $CR_6=NOR_7$, $CONR_8R_9$ and $NR_{10}R_{11}$;
- $R_4$ and $R_5$ together form a fused 5, 6, or 7 membered carbocyclic ring containing at least one heteroatom selected from the group consisting of: O, S, N, and P;
- $R_6$ is selected from the group consisting of: H, $(C_1-C_6)$ alkyl, $(C_2-C_6)$ alkenyl, and $(C_2-C_6)$ alkynyl;
- $R_7$ is selected from the group consisting of H, $(C_1-C_6)$ alkyl, $(C_2-C_6)$ alkenyl, and $(C_1-C_6)$ alkylcarbonyl;
- $R_8$ and $R_9$ are independently selected from the group consisting of: H and $(C_1-C_6)$ alkyl; and
- $R_{10}$ and $R_{11}$ are each independently selected from the group consisting of: H, $(C_1-C_6)$ alkyl, and $(C_1-C_6)$ alkylcarbonyl;
- X, Y, and Z are each independently selected from the group consisting of: H, halo, cyano, thiocyano, isothiocyano, and $(C_1-C_6)$alkylsulfonyloxy, provided that at least one of X, Y, and Z is selected from the group consisting of: halo, cyano, thiocyano, isothiocyano, and $(C_1-C_6)$alkylsulfonyloxy.

2. The compound of claim 1 wherein:
- $R_1$ and $R_2$ are each independently selected from the group consisting of: $(C_1-C_6)$ alkyl;
- $R_3$ is selected from the group consisting of: H, halo, cyano, $(C_1-C_6)$ alkyl, nitro, and $CR_6=NOR_7$;
- $R_4$ and $R_5$ together form a fused 5, 6, or 7 membered carbocyclic ring containing at least one heteroatom selected from the group consisting of: O, S, N, and P;
- $R_6$ is H;
- $R_7$ is $(C_1-C_6)$ alkyl; and
- X, Y, and Z are each independently selected from the group consisting of: H, halo, thiocyano, isothiocyano, and $(C_1-C_6)$ alkylsulfonyloxy, provided that at least one of X, Y, and Z is selected from the group consisting of: halo, thiocyano, isothiocyano, and $(C_1-C_6)$ alkylsulfonyloxy.

3. The compound of claim 1 wherein:
- $R_1$ and $R_2$ are each independently selected from the group consisting of $(C_1-C_3)$ alkyl;
- $R_3$ is selected from the group consisting of: H, halo, cyano, $(C_1-C_6)$ alkyl, nitro, and $CR_6=NOR_7$;
- $R_4$ and $R_5$ together form a fused 5, 6, or 7 membered carbocyclic ring containing at least one heteroatom selected from the group consisting of: O, S, N, and P;
- $R_6$ is H;
- $R_7$ is $CH_3$;
- X, Y, and Z are each independently selected from the group consisting of: H, halo, thiocyano, isothiocyano, provided that at least two of X, Y, and Z are H.

4. The compound of claim 1 wherein:
- $R_1$ is $CH_3$ and $R_2$ is $CH_2CH_3$;
- $R_3$ is selected from the group consisting of: H, halo, cyano, $(C_1-C_6)$ alkyl, nitro, and $CR_6=NOR_7$;
- $R_4$ and $R_5$ together form a fused 5, 6, or 7 membered carbocyclic ring containing at least one heteroatom selected from the group consisting of: O, S, N, and P;
- $R_6$ is H; $R_7$ is $CH_3$; two of X, Y, and Z are H and one of X, Y, and Z is Cl.

5. A compound having the formula:

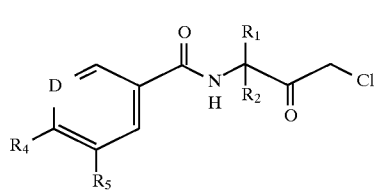

wherein:

D is selected from the group consisting of N and C—R₃;

R₁ is selected from the group consisting of: H, (C₁–C₆) alkyl, (C₁–C₆) haloalkyl, (C₂–C₆) alkenyl, and (C₂–C₆) alkynyl;

R₂ is selected from the group consisting of: (C₁–c₆) alkyl, (C₁–c₆) haloalkyl, (C₂–C₆) alkenyl, and (C₂–C₆) alkynyl;

R₃ is selected from the group consisting of: H, halo, cyano, (C₁–C₆)alkyl, (C₁–C₆) haloalkyl, (C₂–C₆) alkenyl, (C₂–C₆) alkynyl, (C₁–C₆)alkoxy, (C₁–C₆) haloalkoxy, nitro, carboxyl, NHCOOR₆, CR₆=NOR₇, CONR₈R₉ and NR₁₀R₁₁;

R₄ and R₅ together form a fused 5, 6, or 7 membered carbocyclic ring containing at least one heteroatom selected from the group consisting of: O, S, N, and P;

R₆ is selected from the group consisting of: H, (C₁–C₆) alkyl, (C₂–C₆) alkenyl, and (C₂–C₆) alkynyl;

R₇ is selected from the group consisting of: H, (C₁–C₆) alkyl, (C₂–C₆) alkenyl, and (C₁–C₆) alkylcarbonyl;

R₈ and R₉ are independently selected from the group consisting of: H and (C₁–C₆) alkyl; and R₁₀ and R₁₁ are each independently selected from the group consisting of: H, (C₁–C₆) alkyl, and (C₁–C₆) alkylcarbonyl.

6. A compound having the formula:

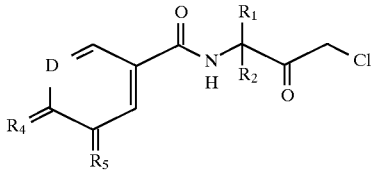

wherein:

D is selected from the group consisting of N and C—R₃;

R₁ is selected from the group consisting of: H, (C₁–C₆) alkyl, (C₁–C₆) haloalkyl, (C₂–C₆) alkenyl, and (C₂–C₆) alkynyl;

R₂ is selected from the group consisting of: (C₁–C₆) alkyl, (C₁–C₆) haloalkyl, (C₂–C₆) alkenyl, and (C₂–C₆) alkynyl;

R₃ is selected from the group consisting of: H, halo, cyano, (C₁–C₆)alkyl, (C₁–C₆) haloalkyl, (C₂–C₆) alkenyl, (C₂–C₆) alkynyl, (C₁–C₆)alkoxy, (C₁–C₆) haloalkoxy, nitro, carboxyl, NHCOOR₆, CR₆=NOR₇, CONR₈R₉ and NR₁₀R₁₁;

R₄ and R₅ together form a fused 5, 6, or 7 membered carbocyclic ring containing at least one heteroatom selected from the group consisting of: O, S, N, and P;

R₆ is selected from the group consisting of: H, (C₁–C₆) alkyl, (C₂–C₆) alkenyl, and (C₂–C₆) alkynyl;

R₇ is selected from the group consisting of H, (C₁–C₆) alkyl, (C₂–C₆) alkenyl, and (C₁–C₆) alkylcarbonyl;

R₈ and R₉ are independently selected from the group consisting of: H and (C₁–C₆) alkyl; and R₁₀ and R₁₁ are each independently selected from the group consisting of: H, (C₁–C₆) alkyl, and (C₁–C₆) alkylcarbonyl.

7. A compound having the formula:

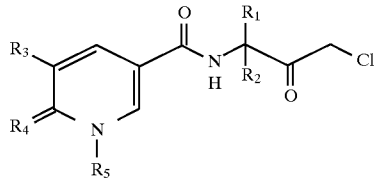

wherein:

R₁ is selected from the group consisting of H, (C₁–C₆) alkyl, (C₁–C₆) haloalkyl, (C₂–C₆) alkenyl, and (C₂–C₆) alkynyl;

R₂ is selected from the group consisting of: (C₁–C₆) alkyl, (C₁–C₆) haloalkyl, (C₁–c₆) alkenyl, and (C₂–C₆) alkynl;

R₃ is selected from the group consisting of: H, halo, cyano, (C₁–C₆)alkyl, (C₁–C₆) haloalkyl, (C₁–C₆) alkenyl, (C₁–C₆) alkynyl, (C₁–C₆)alkoxy, (C₁–C₆) haloalkoxy, nitro, carboxy, NHCOOR₆, CR₆=NOR₇, CONR₈R₉ and NR₁₀R₁₁;

R₄ and R₅ together form a fused 5, 6, or 7 membered carbocyclic ring containing at least one heteroatom selected from the group consisting of: O, S, N, and P;

R₆ is selected from the group consisting of: H, (C₁–C₆) alkyl, (C₂–C₆) alkenyl, and (C₂–C₆) alkynyl;

R₇ is selected from the group consisting of: H, (C₁–C₆) alkyl, (C₂–C₆) alkenyl, and (C₁–C₆) alkylcarbonyl;

R₈ and R₉ are independently selected from the group consisting of: H and (C₁–C₆) alkyl; and R₁₀ and R₁₁ are each independently selected from the group consisting of: H, (C₁–C₆) alkyl, and (C₁–C₆) alkylcarbonyl.

8. A method for controlling phytopathogenic fungi comprising applying to the locus of a plant the compound of claim 1.

9. The method of claim 8 wherein:

R₁ is CH₃ and R₂ is CH₂CH₃;

R₃ is selected from the group consisting of: H, halo, cyano, (C₁–C₆) alkyl, nitro, and CR₆=NOR₇;

R₄ and R₅ together form a fused 5, 6, or 7 membered carbocyclic ring containing at least one heteroatom selected from the group consisting of: O, S, N, and P; R₆ is H; R₇ is CH₃; two of X, Y, and Z are H and one of X, Y, and Z is Cl.

10. A method for controlling phytopathogenic fungi comprising applying to the locus of a plant the compound of claim 5.

11. A method for controlling phytopathogenic fungi comprising applying to the locus of a plant the compound of claim 6.

12. A method for controlling phytopathogenic fungi comprising applying to the locus of a plant the compound of claim 7.

13. A fungicidal composition comprising at least one compound according to claim 1 and at least one compound selected from the group consisting of fungicides and insecticides.

14. A fungicidal composition comprising at least one compound according to claim 5 and at least one compound selected from the group consisting of fungicides and insecticides.

15. A fungicidal composition comprising at least one compound according to claim 6 and at least one compound selected from the group consisting of fungicides and insecticides.

16. A fungicidal composition comprising at least one compound according to claim 7 and at least one compound selected from the group consisting of fungicides and insecticides.

* * * * *